United States Patent [19]

Suga

[11] 4,311,462
[45] Jan. 19, 1982

[54] DENTURES

[76] Inventor: Goro Suga, 1835 N. King St., Honolulu, Hi. 96819

[21] Appl. No.: 147,743

[22] Filed: May 8, 1980

[51] Int. Cl.³ ............................................. A61C 13/24
[52] U.S. Cl. ..................................... 433/184; 433/172
[58] Field of Search ............... 433/184, 172, 167, 171, 433/177, 185, 186, 187, 188

[56] References Cited

U.S. PATENT DOCUMENTS

| 78,070 | 5/1868 | David | 433/184 |
| 810,184 | 1/1906 | Broadbent | 433/184 |
| 1,201,177 | 10/1916 | Hanscom | 433/172 |
| 2,250,373 | 7/1941 | Hagerman | 433/177 |
| 2,770,880 | 11/1956 | Sherrod | 433/177 |
| 3,623,225 | 11/1971 | Moore | 433/184 |

FOREIGN PATENT DOCUMENTS

| 1423030 | 12/1966 | France | 433/185 |
| 106010 | 5/1917 | United Kingdom | 433/184 |

OTHER PUBLICATIONS

"The Use of Elastic and Resilient . . . ", by Tylman, Dental Digest, Apr. 1943, pp. 167, 168.

"Current Clinical Dental Terminology", Boucher, 1974, pp. 363, 378.

Primary Examiner—Gene Mancene
Assistant Examiner—John J. Wilson
Attorney, Agent, or Firm—Shlesinger, Fitzsimmons & Shlesinger

[57] ABSTRACT

It has been found that the upper and lower dentures of false teeth tend to remain more securely in place if the marginal edges of the outer flange, in the case of the upper denture, and the inner flange, in the case of the lower denture, are thickened in the posterior areas of the respective plate. In the case of the upper denture, the marginal edge of the upper flange is curved sharply outwardly so as to engage the cheek of the wearer, during use, in the vicinity of the junction of the cheek with upper gum. This thickened marginal portion of the flange is greater in the posterior areas than in the anterior area of the plate. In the case of the lower plate, the posterior ends of the inner flange rearwardly from the second molars, are provided with inwardly and downwardly extending projections which, during use, extend beneath opposite sides of a person's tongue adjacent the rear thereof, and into engagement with the floor of the person's mouth.

3 Claims, 7 Drawing Figures

DENTURES

This invention relates to false teeth or dentures, and more particularly to improved dentures that are designed to provide better natural retention in a person's mouth, as compared to prior, conventional dentures.

A recurring problem for denture wearers relates to the difficulty in maintaining the upper and/or lower plates securely in place during use. Although there are various paste products on the market which can be used to help adhere the plates to a person's gums, such products merely supplement the suction-type adhesion which should occur as the result of properly designed plates.

The design of dental plates of the type described is considerably limited not only by the configuration of one's mouth, but also because of the need for minimizing discomfort to the wearer. In other words, while it might be possible to design plates of the type described so they will securely fit and remain in place, when in use, the increased property of adherence normally is accompanied by a corresponding increase in the discomfort of the wearer.

Certain conventional dentures, for example, have been designed to be flexible, as in U.S. Pat. No. 2,770,880, while others (see U.S. Pat. Nos. 1,970,474 and 1,201,177) have relied upon lateral projections on denture plate flanges to help hold them in place during use. Still others have employed a resilient or yielding material in making the plates (see U.S. Pat. No. 2,250,373), but because of improper design these efforts have not solved the problem of loose denture plates.

It is an object of this invention, therefore, to provide an improved dental plate of the type described which embodies improved plate flanges which cause the associated plate to remain securely in place during use.

Another object of this invention is to provide both improved upper and lower dental plates of the type described which utilize relatively thick plate flanges the marginal edges of which are carefully shaped to improve the natural adhesion of the plates of the gum to a wearer, when in use.

Other objects of this invention will be apparent hereinafter from the specification and from the recital of the appended claims, particularly when read in conjunction with the accompanying drawing.

Figure 1:
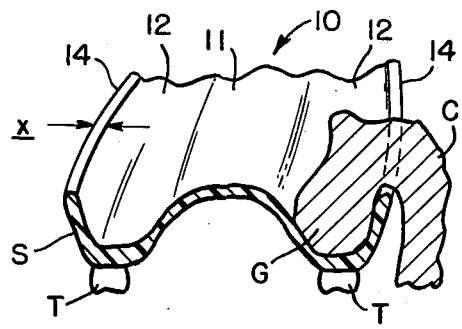
FIG. 1 is a fragmentary sectional view taken transversely through a conventional, upper dental plate illustrating the configuration of the flange which surrounds the plate to embrace the outer edge of the wearer's upper gum, part of the plate being shown in perspective.

Referring now to the drawing by numerals of reference, in FIG. 1 the numeral 10 denotes a conventional or known upper dental plate having the usual central area 11 which is disposed to be engaged with the roof of a person's mouth, and recessed areas 12 disposed to accommodate the upper gums G of the wearer. Two of the false teeth which are secured to the underside of the recessed areas 12 in the usual manner are denoted at T; and 14 denotes the usual upstanding peripheral flange or rim which forms the outer boundary of the recesses 12, and which is engagable around the outer peripheral surface of the upper gum G of the wearer in the space between the gum and cheek C of the wearer. Normally this flange 14 is of a uniform thickness X, for example approximately 2 mm. around the entire rim of the plate. Also, the outer, curvilinear surface S of the flange 14 is generally uniformly curved in the same direction about the recess 12 in the plate, so that the upper edge of the flange 14 confronts the junction between the gum G and cheek C of the wearer as shown in FIG. 1.

Figure 3:
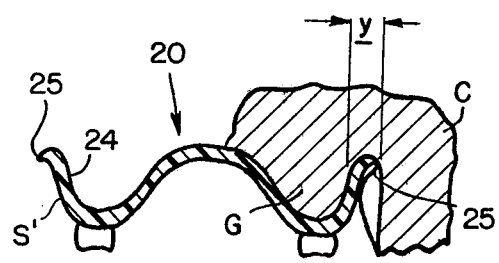
FIG. 3 is a fragmentary sectional view taken generally along the line 3—3 in FIG. 2 looking in the direction of the arrows, and illustrating fragmentarily and in section a portion of a person's gum and cheek as they would appear when engaged with this improved plate.
Figure 4:
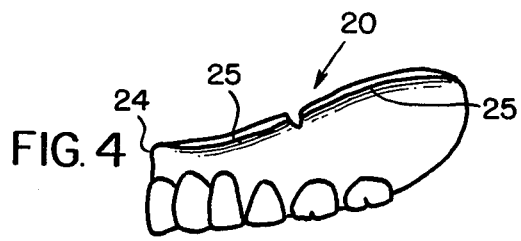
FIG. 4 is a side elevational view of this upper plate.
Figure 2:
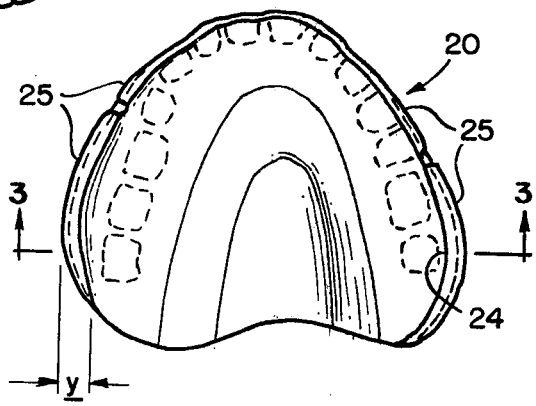
FIG. 2 is a plan view of an improved upper denture plate of a type made according to one embodiment of this invention.

As distinguished from this construction, applicant has found that substantially increased dental plate retention can be experienced if the flange of an upper denture is made thicker than normal, and is found with a compound outer surface S'. The upper denture plate denoted generally by the numeral 20 in FIGS. 2, 3 and 4, for example, is an improved plate in which the flange 24 thereof, which corresponds to the flange 14 of a conventional plate, has a thickness y (FIGS. 2 and 3), which is greater than that of the usual thickness X of the conventional plate. The thickness y may be, for example, on the order about ⅛" to ¼" in the posterior area of flange 24, and somewhat less thicker in the anterior or forward area of this flange. (As used herein, posterior means the areas of the flanges located, when in use, in the back of a person's mouth, while the anterior areas refer to those areas of the plate which face forwardly or toward the opening of a person's mouth.)

In addition to being thicker than prior such flanges, the flange 24 is formed adjacent its upper (FIG. 3) marginal edge with an outwardly curved, cheek-engaging portion 25, which is curved about an axis located exterior to the plate 20, whereby the flange 24 has a compound curvilinear surface S' formed on its outer surface. As shown more clearly by broken lines in FIG. 2, this cheek-engaging portion 25 of the flange 24, which might also be defined as a sharp curvature portion of the flange, is thicker or more pronounced in the postior area of plate 20, and is slightly less pronounced or thinner in the anterior or forward area of the plate. In practice, it has been found that the thickening of the upper edge of the flange 24, and the curving thereof outwardly as at 25, substantially increases the suction which is generated between flange 24 and the surrounding portion of a person's mouth, when the plate 20 is being worn. Moreover, experience has also indicated that this change in the configuration of the conventional flange 14 has not in any way increased the discomfort of the wearer.

Figure 5:
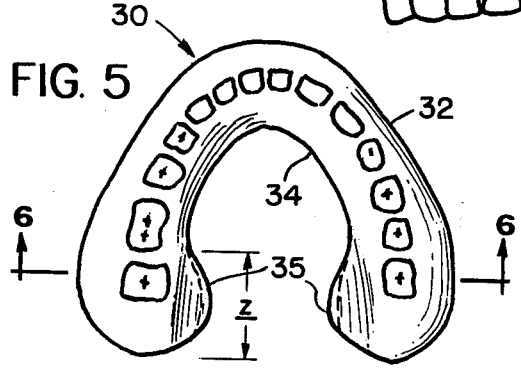
FIG. 5 is a plan view of an improved lower dental plate made according to another embodiment of this invention.
Figure 6:
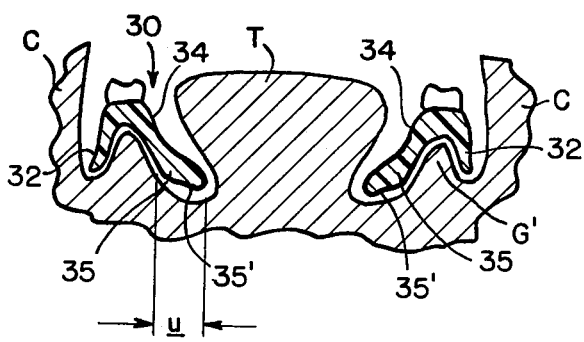
FIG. 6 is a fragmentary sectional view taken generally along the lines 6—6 in FIG. 5 looking in the direction of the arrows, and illustrating also in cross section part of the lower jaw and cheeks of a person as they would appear when this plate is being worn.
Figure 7:
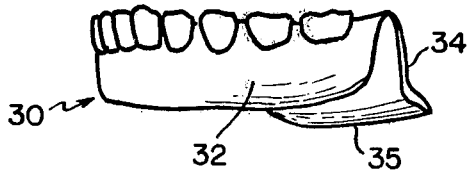
FIG. 7 is a side elevational view of this lower dental plate.

Referring now to FIGS. 5-7, 30 denotes generally an improved lower denture having an outer peripheral flange 32, which is disposed to be seated between a person's cheek C and lower gum G'; and an inner flange 34 which is seated between the gum and a person's tongue T (FIG. 6). This outer flange 32 is sometimes referred to as the lingual flange.

Because of the depth of the jaw bone adjacent to the rear or posterior of a person's mouth, it has been conventional in the past to make the lingual flange of a lower dental plate slightly higher or deeper than the anterior portion of the plate. (See, for example, the above-noted U.S. Pat. No. 2,250,373). Normally, however, these enlarged posterior portions of the lingual flange are designed to embrace the insides of a person's lower gum, and for that purpose normally are curved, as viewed for example in FIG. 6, commonly and inwardly against the base of the gum. Contrary to this conventional construction, applicant's improved dental plate 30 is designed with an enlarged, downwardly inclined lingual flange portion 35 at each posterior end of the plate. Moreover, as shown more clearly in FIGS. 5 and 6, these enlarged flange portions 35 extend downwardly and inwardly beneath opposite sides of the wearer's tongue, so that the tongue will always be in contact with the lingual flange portions 35 when the plate 30 is being worn. With the tongue engaging both of the flange portions 35, during use, the plate 30 is prevented from tilting or rising upwardly out of engagement with the lower gum G' while a person is talking, eating, etc.

The normal contour of the floor of a person's mouth, as well as the associated tongue, are subject to changes when a person talks, eats, etc. The portions 35 of the flange 34 are placed in the back portions of the denture 30 to extend from the posterior of plate 30 forwardly to the points adjacent the second molars (the second lowermost molars as shown in FIG. 5). If the enlarged flange portions 35 were to extend any further toward the front and anteriorly of the plate 30, the person's tongue would tend undesirably to raise or lift the plate upwardly and to dislodge it from its seat during use. E.g., when the tongue retruded posteriorly from its normal position, the lingual flanges would be free and clear from the underside of the tongue, and the floor of the mouth would therefore lift the plate upwardly and dislodge it. It is for these reasons that the flange portions or sections 35 are designed to be disposed adjacent to the rear ends of plate 30.

In practice, each inclined flange portion 35 may have a width u (FIG. 6) of up to approximately $\frac{3}{8}''$, and may have an overall length z (FIG. 5) of approximately $\frac{1}{2}''$ to $\frac{3}{4}''$. Obviously the thickness of a respective flange section 35 will vary from person to person, depending upon among other things, the size of the person's jaw, the height of the gum ridge, etc. The length z of each portion 35 is limited, however, by the fact that such portions should not extend forwardly or anteriorly far enough to bruise the lower portion of the person's mouth, or to interfere with the movement of his or her tongue during the use of the plate.

Improved retention has also been achieved by curving the terminal portion of each enlarged section 35 of a flange abruptly or sharply downwardly to form a recess or scalloped pocket 35' in the underside of the section as shown in FIG. 6. With the terminal edge of each section 35 being engaged with, or depressing the floor of a person's mouth, during use of the plate 30, the pockets 35' appear to increase the suction or retention of the plate in place. This is particularly true as compared to prior such plates, because in the case of applicant's plate 30, the downwardly extending projections 35 remain engaged with the floor of a person's mouth, even when the floor tends to drop during use, so that there is no tendency for the plate 30 to become unseated as the floor of the mouth drops.

From the foregoing it will be apparent that the present invention provides improved means for retaining dentures in place during use. By slight changes in specific areas of the dental plate flanges, applicant has found that it is possible substantially to increase the suction or holding power of both the upper and a lower dental plate in a person's mouth. By thickening the flanges on an upper plate, particularly in the posterior areas, and by curving the marginal portions of the upper edges of the flanges outwardly to form compound, other curvilinear surfaces on the flanges, the natural holding power of such plates has been increased without effecting any corresponding discomfort in the wearer. Also, by utilizing enlarged sections or borders on the lingual flange of a lower plate in the posterior area thereof, similar improved performance has been achieved in connection with a lower dental plate. These lingual flange portions, which extend posteriorly from the second molar areas, and which are inclined to project downwardly into engagement with the floor of a person's mouth during use, and beneath opposite sides of the person's tongue, assure retention of the lower plate in place even when the floor of the person's mouth happens to drop from its normal position during talking, eating, etc. Furthermore, it has been found that these modifications to the lower dental plate can also be made without any resulting discomfort to the wearer.

While this invention has been illustrated and described in detail in connection with only certain embodiments thereof, it will be apparent that it is capable of still further modification, and this application is intended to cover any such modifications as may fall within the scope of one skilled in the art, or the appended claims.

What I claim is:

1. In a denture plate having therein an inverted, generally U-shaped recess for accommodating the lower gum of a wearer, and having thereon a generally arcuate lingual flange forming one boundary of said U-shaped recess, said flange having thereon an inside surface facing on said recess to overlie and embrace the inside of the gum which is seated in said recess, an outside surface generally similar in configuration to said inside surface, and an elongate edge interconnecting said inside and outside surfaces and disposed to extend around said inside of said gum adjacent the base thereof, the improvement comprising, enlarged rim portions formed on said edge of said flange adjacent opposite ends, respectively, of said recess, said flange being substantially wider in the areas of said enlarged rim portions, than in the other areas of said flange, said enlarged rim portions being inclined to said flange so as to project downwardly and inwardly beyond the remaining portions of said edge of said flange, when said plate is in use, thereby slightly to depress and to remain in contact with the floor of a person's mouth during use, said enlarged rim portions extending at each side of said plate rearwardly from the normal position of the second molars to the posterior or rear ends of said flange, and curving downwardly and inwardly towards the center of said lower plate thereby to extend beneath the rear or inner end of a person's tongue when said plate is in use.

2. A denture plate as defined in claim 1, wherein the width of said flange in the area of one of said enlarged rim portions is at least approximately ⅜".

3. A denture plate as defined in claim 1, wherein the length of one of said enlarged rim portions from a second molar position to the adjacent end of said flange is in the range of approximately ½".

* * * * *